United States Patent
Deshmukh et al.

(10) Patent No.: US 7,615,551 B2
(45) Date of Patent: *Nov. 10, 2009

(54) SALICYLATE AND GENTISATE SALTS OF A PIPERAZINE COMPOUND

(75) Inventors: Subodh S. Deshmukh, White Plains, NY (US); Kadum Ali, Congers, NY (US); Christopher R. Diorio, Campbell Hall, NY (US); Wendy Dulin, Tuxedo, NY (US); Eric C. Ehrnsperger, Chestnut Ridge, NY (US); Mahdi B. Fawzi, Morristown, NJ (US); Syed Muzafar Shah, East Hanover, NJ (US)

(73) Assignee: Solvay Pharmaceuticals, B.V. (NL)

( * ) Notice: Subject to any disclaimer, the term of this patent is extended or adjusted under 35 U.S.C. 154(b) by 398 days.

This patent is subject to a terminal disclaimer.

(21) Appl. No.: 11/519,738

(22) Filed: Sep. 12, 2006

(65) Prior Publication Data

US 2007/0060580 A1     Mar. 15, 2007

Related U.S. Application Data

(60) Provisional application No. 60/716,161, filed on Sep. 12, 2005.

(51) Int. Cl.
C07D 413/14     (2006.01)
A61K 31/33      (2006.01)

(52) U.S. Cl. .................................. 514/230.5; 544/105
(58) Field of Classification Search ................. 544/105; 514/230.5
See application file for complete search history.

(56) References Cited

U.S. PATENT DOCUMENTS

| | | | |
|---|---|---|---|
| 4,438,119 | A | 3/1984 | Allen et al. |
| 4,687,772 | A | 8/1987 | Alderdice |
| 4,771,053 | A | 9/1988 | Cott et al. |
| 5,162,375 | A | 11/1992 | Nicholson et al. |
| 5,824,680 | A | 10/1998 | Turner et al. |
| 2005/0215526 | A1 | 9/2005 | Hulme et al. |
| 2007/0059366 | A1 | 3/2007 | Ali et al. |
| 2007/0060580 | A1 | 3/2007 | Deshmukh et al. |
| 2007/0254876 | A1 | 11/2007 | Deshmukh et al. |

FOREIGN PATENT DOCUMENTS

| | | | |
|---|---|---|---|
| WO | WO 93/04681 | A1 | 3/1993 |
| WO | WO 00/16777 | A1 | 3/2000 |
| WO | WO 00/43378 | A | 7/2000 |
| WO | WO 00/43378 | A1 | 7/2000 |
| WO | WO 01/14330 | A2 | 3/2001 |
| WO | WO 01/52855 | A2 | 7/2001 |
| WO | WO 02/066473 | A1 | 8/2002 |
| WO | WO 2005/061493 | A2 | 7/2005 |
| WO | WO 2007/033191 | A1 | 3/2007 |
| WO | WO 2007/033192 | A1 | 3/2007 |
| WO | WO 2007/033193 | A2 | 3/2007 |
| WO | WO 2007/033193 | A3 | 3/2007 |

OTHER PUBLICATIONS

Lander et al. Nature 409:860 (2001).
Das and Khan. Prostaglandins Leukot Essent Fatty Acids 58:165 (1998).
Ungerstedt. Acta Physiol. Scand. 82: (suppl. 367) 69 (1971).
Sedvall et al. The Lancet, 346:743-749, (1995).
Hietala. The Lancet, 346:1130-1131 (1995).
Kemppainen et al. Eur J Neurosci., 18:149-154 (2003).
Kleven et al. European Journal of Pharmacology, 281:219-228 (1995).
Leone et al. Neuro Report, 9:2605-2608 (1998).
De Vry et al. European Journal of Pharmacology, 357:1-8 (1998).
Wolff et al. European Journal of Pharmacology, 340:217-220 (1997).
Alfieri et al. British Journal of Cancer, 72:1013-1015 (1995).
Wolff et al., Pharmacology Biochemistry and Behavior, 52:571-575 (1995).
Lucot. European Journal of Pharmacology, 253:53-60 (1997).
Rasmussen et al. Annual Reports in Medicinal Chemistry, 30:1-9 (1995).
Millan, Journal of Pharmacology and Experimental Therapeutics, 295:853-861 (2000).
Berge et al. "Pharmaceutical Salts," Journal of Pharmaceutical Sciences, vol. 66, No. 1, Jan. 1977, pp. 1-19.
Hagger, et al. Biol. Psychiatry, 34:702 (1993).
Sharma et al. J. Clin. Psychopharmacol., 18:128 (1998).
Lee et al. J. Clin. Psychiatry, 55:82 (1994).
Fujii, et al. J. Neuropsychiatry Clin. Neurosci., 9:240 (1997).
Mason et al. Eur. J. Pharmacol., 221:397 (1992).
Newman-Tancredi et al. Neuropharmacology, 35:119, (1996).
Sumiyoshi et al. J. Clin. Pharmacol., 20:386 (2000).
Carli et al. Eur. J. Neurosci., 10:221 (1998).
Meneses et al. Neurobiol. Learn. Mem., 71:207 (1999).
Glennon et al. Neuroscience and Behavioral Reviews, 14:3547 (1990).
Masson et al. Pharm. Rev. 51:439 (1999).
Van Der Heyden and Bradford. Behav. Brain Res. 31:61 (1988).
Van Der Poel et al. Psychopharmacology, 97:147 (1989).
International Search Report for PCT/US2006/035519, Date of mailing:Dec. 7, 2006.

(Continued)

*Primary Examiner*—Kahsay T Habte
(74) *Attorney, Agent, or Firm*—Finnegan, Henderson, Farabow, Garrett & Dunner, LLP

(57) ABSTRACT

The present invention provides salt forms, and compositions thereof, useful as modulators of one or more GPCRs and which exhibit desirable characteristics for the same.

25 Claims, 7 Drawing Sheets

OTHER PUBLICATIONS

Office Action mailed Feb. 2, 2009, in co-pending U.S. Appl. No. 11/519,763.

Office Action mailed Apr. 9, 2008, in co-pending U.S. Appl. No. 11/519,756.

Office Action mailed Oct. 24, 2008, in co-pending U.S. Appl. No. 11/519,756.

Peak Search Report (13 Peaks, Max P/N = 5.7)
[94-185-1.RAW]
PEAK: 37-pts/Parabolic Filter, Threshold=9.0, Cutoff=0.1%, BG=3/1.0, Peak-Top=Summr

| 2-Theta | d(Å) | BG | Height | I% | Area | I% | FWHM |
|---|---|---|---|---|---|---|---|
| 7.239 | 12.2009 | 52 | 74 | 44 | 1463 | 22.5 | 0.158 |
| 8.2 | 10.774 | 53 | 167 | 99.4 | 2836 | 43.6 | 0.144 |
| 8.999 | 9.819 | 53 | 70 | 41.7 | 1089 | 16.7 | 0.124 |
| 10.799 | 8.186 | 50 | 123 | 73.2 | 4043 | 62.1 | 0.279 |
| 16.422 | 5.3935 | 41 | 68 | 40.5 | 2058 | 31.6 | 0.242 |
| 18.03 | 4.9158 | 47 | 40 | 23.8 | 877 | 13.5 | 0.175 |
| 19.05 | 4.6549 | 49 | 168 | 100 | 6510 | 100 | 0.329 |
| 20.191 | 4.3943 | 51 | 77 | 45.8 | 2664 | 40.9 | 0.277 |
| 21.47 | 4.1353 | 49 | 71 | 42.3 | 1960 | 30.1 | 0.221 |
| 24.301 | 3.6596 | 41 | 45 | 26.8 | 1306 | 20.1 | 0.232 |
| 24.925 | 3.5694 | 41 | 33 | 19.6 | 513 | 7.9 | 0.124 |
| 27.992 | 3.1849 | 34 | 29 | 17.3 | 726 | 11.2 | 0.2 |
| 29.68 | 3.0075 | 33 | 31 | 18.5 | 521 | 8 | 0.134 |

FIG. 1b

| Peak Search Report (36 Peaks, Max P/N = 25.9) | | | | | | | |
|---|---|---|---|---|---|---|---|
| [94-192-1.RAW] | | | | | | | |
| PEAK: 21-pts/Parabolic Filter, Threshold=9.0, Cutoff=0.1%, BG=3/1.0, Peak-Top=Summ | | | | | | | |
| 2-Theta | d(Å) | BG | Height | I% | Area | I% | FWHM |
| 8.158 | 10.8283 | 258 | 1023 | 33 | 12473 | 18.2 | 0.207 |
| 8.96 | 9.861 | 261 | 402 | 13 | 3959 | 5.8 | 0.167 |
| 9.923 | 8.9064 | 288 | 155 | 5 | 1706 | 2.5 | 0.176 |
| 10.762 | 8.2141 | 291 | 599 | 19.3 | 7235 | 10.5 | 0.205 |
| 11.581 | 7.6348 | 295 | 615 | 19.9 | 6800 | 9.9 | 0.188 |
| 12.701 | 6.9639 | 285 | 495 | 16 | 5409 | 7.9 | 0.186 |
| 13.479 | 6.5638 | 284 | 310 | 10 | 8169 | 11.9 | 0.448 |
| 13.782 | 6.42 | 286 | 1127 | 36.4 | 14833 | 21.6 | 0.224 |
| 14.762 | 5.9961 | 281 | 408 | 13.2 | 8808 | 12.8 | 0.367 |
| 16.478 | 5.3751 | 272 | 1341 | 43.3 | 15549 | 22.6 | 0.197 |
| 18.038 | 4.9138 | 463 | 555 | 17.9 | 7295 | 10.6 | 0.223 |
| 18.421 | 4.8123 | 270 | 706 | 22.8 | 8616 | 12.5 | 0.207 |
| 19.08 | 4.6476 | 474 | 2858 | 92.3 | 47043 | 68.5 | 0.28 |
| 20 | 4.4358 | 470 | 1729 | 55.8 | 61899 | 90.1 | 0.609 |
| 20.259 | 4.3798 | 480 | 3096 | 100 | 68697 | 100 | 0.377 |
| 20.7 | 4.2874 | 515 | 1832 | 59.2 | 17550 | 25.5 | 0.163 |
| 21.46 | 4.1374 | 446 | 1472 | 47.5 | 32680 | 47.6 | 0.377 |
| 21.879 | 4.059 | 397 | 1439 | 46.5 | 48780 | 71 | 0.576 |
| 23.319 | 3.8115 | 376 | 620 | 20 | 8337 | 12.1 | 0.229 |
| 24.278 | 3.663 | 395 | 1156 | 37.3 | 18788 | 27.3 | 0.276 |
| 24.981 | 3.5615 | 387 | 2236 | 72.2 | 23209 | 33.8 | 0.176 |
| 25.603 | 3.4764 | 373 | 267 | 8.6 | 3734 | 5.4 | 0.238 |
| 26.198 | 3.3988 | 392 | 291 | 9.4 | 3060 | 4.5 | 0.179 |
| 26.94 | 3.3068 | 395 | 596 | 19.3 | 7614 | 11.1 | 0.217 |
| 27.662 | 3.2221 | 364 | 358 | 11.6 | 4900 | 7.1 | 0.233 |
| 28.042 | 3.1793 | 330 | 620 | 20 | 7483 | 10.9 | 0.205 |
| 29.161 | 3.0599 | 329 | 679 | 21.9 | 16637 | 24.2 | 0.417 |
| 29.54 | 3.0214 | 354 | 1018 | 32.9 | 19002 | 27.7 | 0.317 |
| 29.862 | 2.9895 | 420 | 488 | 15.8 | 4331 | 6.3 | 0.151 |
| 31.7 | 2.8203 | 271 | 464 | 15 | 9473 | 13.8 | 0.347 |
| 32.056 | 2.7897 | 263 | 243 | 7.8 | 3625 | 5.3 | 0.254 |
| 32.801 | 2.7281 | 260 | 375 | 12.1 | 7637 | 11.1 | 0.346 |
| 36.48 | 2.4609 | 248 | 236 | 7.6 | 4538 | 6.6 | 0.327 |
| 37.019 | 2.4264 | 254 | 219 | 7.1 | 4358 | 6.3 | 0.338 |
| 38.279 | 2.3494 | 264 | 297 | 9.6 | 6257 | 9.1 | 0.358 |
| 38.758 | 2.3214 | 268 | 215 | 6.9 | 3371 | 4.9 | 0.267 |

FIG. 2b

SALICYLATE AND GENTISATE SALTS OF A PIPERAZINE COMPOUND

CROSS-REFERENCE TO RELATED APPLICATION

This application claims the benefit of priority from U.S. Provisional Patent Application Ser. No. 60/716,161, filed on Sep. 12, 2005, the entirety of which is hereby incorporated herein by reference.

FIELD OF THE INVENTION

The present invention provides salt forms, and compositions thereof, useful as modulators of one or more GPCRs.

BACKGROUND OF THE INVENTION

The G-protein coupled receptor (GPCR) family is the largest known gene family representing greater than 1% of the human genome, and encompassing a wide range of biological functions (including various autocrine, paracrine and endocrine processes). The GPCR superfamily is also the most exploited gene family by the pharmaceutical industry for the development of therapeutic compounds. GPCRs have been categorized into rhodopsin-like GPCRs, the secretin-like GPCRs, the cAMP receptors, the fungal mating pheromone receptors, and the metabotropic glutamate receptor family. The rhodopsin-like GPCRs themselves represent a widespread protein family that includes hormone, neurotransmitter and light receptors, all of which transduce extracellular signals through interaction with guanine nucleotide-binding (G) proteins. Although their activating ligands vary widely in structure and character, the amino acid sequences of rhodopsin-like GPCRs are very similar and are believed to adopt a common structural framework comprising 7 transmembrane (TM) spanning a-helices and are coupled to G-proteins within the cell which dissociate from the receptor on agonist binding and initiate or inhibit secondary messenger signalling mechanisms. See: Lander et al. Nature 409:860 (2001); Basic and clinical pharmacology, $8^{th}$ Ed., Katzung. USA: The McGraw Hill Companies, Inc. (2001).

The rhodopsin-like GPCR family includes several classes of receptors which are variously distributed throughout the central nervous system (CNS) and many peripheral sites and have been implicated in a variety of CNS and neuropsychiatric conditions. Included among these receptors are dopamine ("D") receptors, and 6 of 7 main subtypes of serotonin (5-hydroxytryptamine, "5HT") receptors (5HT$_{1, 2}$ and $_{4-7}$ receptor subtypes are GPCRs while the 5HT$_3$ receptor subtypes are ligand-gated Na$^+$/K$^+$ ion channel).

Dopamine neurons in the vertebrate central nervous system are involved in the initiation and execution of movement, the maintenance of emotional stability, and the regulation of pituitary function. Dopamine binding to the extracellular binding groove of D receptors activates G-proteins—the D$_1$ and D$_5$ receptor subtypes ("D$_1$-like") are linked to stimulatory G-proteins, whereas receptor subtypes 2-4 ("D$_2$-like") are linked to inhibitory G-proteins. D$_2$-like receptors are found through out the brain and in smooth muscle and presynaptic nerve terminals and have an inhibitory effect on neurotransmission when bound by an agonist. Specifically, D$_2$ receptors are abundant and widespread in the striatum, limbic system, thalamus, hypothalamus, and pituitary gland). Antagonist binding to D$_2$ receptors inhibits agonist binding and therefore prevents the inhibition of down-stream signalling mechanisms. Antagonists of D$_2$ receptors are used in the treatment of psychoses (e.g., schizophrenia, mania, psychotic depression, and bipolar disorder), and show utility for short-term sedation in aggression or agitation (e.g., amisulpride, clozapine, haloperidol, nemonapride, pimozide, remoxipride, spiperone, sulpiride) and may be useful for treating drug addiction, while agonists of D$_2$ receptors are used in the treatment of Parkinson's disease and to suppress prolactin secretion arising from tumours of the pituitary gland (e.g., apomorphine, bromocriptine, dihydroergotamine, piribedil, quinpirole), and to treat restless legs syndrome (RLS; e.g., pramipexole, ropinirole). See: Basic and clinical pharmacology, $8^{th}$ Ed., Katzung. USA: The McGraw Hill Companies, Inc. (2001); Pharmacology, $4^{th}$ Ed., Rang et al. Edinburgh, UK: Harcourt Publishers Ltd. (2001); Sedvall et al. The Lancet, 346:743-749, (1995); Hietala. The Lancet, 346:1130-1131 (1995); Kemppainen et al. Eur J Neurosci., 18:149-154 (2003)

5-Hydroxytryptamine is ubiquitous in plants and animals. It is an important neurotransmitter and local hormone in the CNS and intestine, and is implicated in a vast array of physiological and pathophysiological pathways. 5-Hydroxytryptamine binding to the extracellular binding groove of 5HT receptors activates G-proteins—the 5HT$_1$ receptor subtypes are known to be linked to inhibitory G-proteins, whereas subtypes 2, 4, 6 and 7 are known to be linked to stimulatory G-proteins. Of these, 5HT$_1$ receptor subtypes (at least 5 are known) are known to occur primarily in the brain and cerebral blood vessels where they mediate neural inhibition and vasoconstriction. Specific agonists at 5HT$_1$ receptors are used in migraine therapy (e.g., sumatriptan) and in the treatment of stress/anxiety (e.g., buspirone), while antagonists have been recommended in the treatment of psychoses (e.g., spiperone, methiothepin). Additionally, regulation of the 5HT$_1$ receptor subtypes have been implicated in drug addiction, Alzheimer's disease, Parkinson's disease, depression, emesis, and eating disorders. 5HT$_2$ receptor subtypes (at least 3 are known) are found throughout the CNS and at many peripheral sites where they produce excitatory neuronal and smooth muscle effects. 5HT$_2$ receptor antagonists are employed in migraine therapy (e.g., methisergide) and have shown potential in the treatment of scleroderma and Raynaud's phenomenon (e.g., ketanserin). 5HT$_3$ receptors are known to occur mainly in the peripheral nervous system and antagonists are employed as anti-emetics (e.g., ondansetron, tropisetron). 5HT$_4$ receptors are found in the brain, as well as the heart, bladder and gastrointestinal (GI) tract. Within the GI tract they produce neuronal excitation and mediate the effect of 5HT in stimulating peristalsis. Specific 5HT$_4$ receptor antagonists are used for treating GI disorders (e.g., metoclopramide). 5HT receptor subtypes 5 (at least 5 are known), 6, and 7 are also found throughout the CNS and may be potential targets for small-molecule drugs. In particular, the 5HT$_7$ receptor subtype has been implicated in depression, psychoses, Parkinson's disease, Alzheimer's disease, Huntington's disease, migraine, stress/anxiety, eating disorders, and emesis. See: Basic and clinical pharmacology, $8^{th}$ Ed., Katzung. USA: The McGraw Hill Companies, Inc. (2001); Pharmacology, $4^{th}$ Ed., Rang et al. Edinburgh, UK: Harcourt Publishers Ltd. (2001); Kleven et al. European Journal of Pharmacology, 281:219-228 (1995); U.S. Pat. No. 5,162,375; Leone et al. Neuro Report, 9:2605-2608(1998); U.S. Pat. No. 4,771,053; WO 01/52855; De Vry et al. European Journal of Pharmacology, 357:1-8 (1998); Wolff et al. European Journal of Pharmacology, 340:217-220 (1997); Alfieri et al. British Journal of Cancer, 72:1013-1015 (1995); Wolff et al., Pharmacology Biochemistry and Behavior, 52:571-575 (1995); Lucot. European Journal of Pharmacology, 253:53-60 (1997); U.S. Pat. No. 5,824,680; U.S. Pat. No. 4,687,772; Rasmussen et al. Annual Reports in Medicinal Chemistry, 30:1-9 (1995); WO 00/16777; U.S. Pat. No. 4,438,119; Millan, Journal of Pharmacology and Experimental Therapeutics, 295:853-861 (2000); WO 93/04681; Miyamoto, et al. Current Opinion in CPNS Investigational Drugs, 2:25 (2000); Hagger, et al. Biol. Psychiatry, 34:702 (1993); Sharma et al. J. Clin. Psychopharmacol., 18:128 (1998); Lee et al. J. Clin. Psychiatry, 55:82 (1994); Fujii, et al. J. Neuropsychiatry Clin. Neurosci., 9:240 (1997); Mason et al. Eur. J. Pharmacol., 221:397 (1992); Newman-Tancredi et al. Neuropharmacology, 35:119, (1996); Sumiyoshi et al. J. Clin. Pharmacol., 20:386 (2000); Carli et al. Eur. J. Neurosci., 10:221 (1998); Meneses et al. Neurobiol. Learn. Mem., 71:207 (1999); and Glennon et al. Neuroscience and Behavioral Reviews, 14:3547 (1990).

The action of 5HT at synapses is terminated by its $Na^+/K^+$-mediated reuptake across the pre-synaptic membrane. 5HT-reuptake inhibitors are employed in the treatment of depression, stress/anxiety, panic disorder, obsessive compulsive disorder, eating disorders, and social phobias, (e.g., citalopram, clomipramine, fluoxetine, fluvoxamine, indatraline, zimelidine) and may be useful in the treatment of migraine, psychoses, Alzheimer's disease, Parkinson's disease, Huntington's disease, drug addiction, eating disorders, scleroderma and Raynauds phenomenon, GI tract disorders related to the regulation of peristalsis, and/or emesis. See: Basic and clinical pharmacology, 8th Ed., Katzung. USA: The McGraw Hill Companies, Inc. (2001); Pharmacology, 4th Ed., Rang et al. Edinburgh, UK: Harcourt Publishers Ltd. (2001); Masson et al. Pharm. Rev. 51:439 (1999); and additionally, the references in the preceding paragraphs.

Accordingly, it would be desirable to provide compounds which modulate GPCRs in a form suitable for administration to a patient in need of treatment for any of the above-mentioned disorders. In particular, it would be desirable for such compounds to exhibit additional characteristics such as good solubility, stability and ease of formulation, etc.

SUMMARY OF THE INVENTION

It has now been found that the novel salt forms of the present invention, and compositions thereof, are useful as modulators of one or more GPCRs and exhibit desirable characteristics for the same. In general, these salt forms, and pharmaceutically acceptable compositions thereof, are useful for treating or lessening the severity of a variety of diseases or disorders including, but not limited to, Parkinson's disease, psychoses (e.g., schizophrenia, mania, psychotic depression, and bipolar disorder), depression, stress/anxiety, Alzheimer's disease, Huntington's disease, panic disorder, obsessive compulsive disorder, eating disorders, drug addiction, social phobias, aggression or agitation, migraine, scleroderma and Raynaud's phenomenon, emesis, GI tract disorders related to the regulation of peristalsis, RLS, and prolactin secretion arising from tumours of the pituitary gland.

DETAILED DESCRIPTION OF THE INVENTION

Figure 1A:
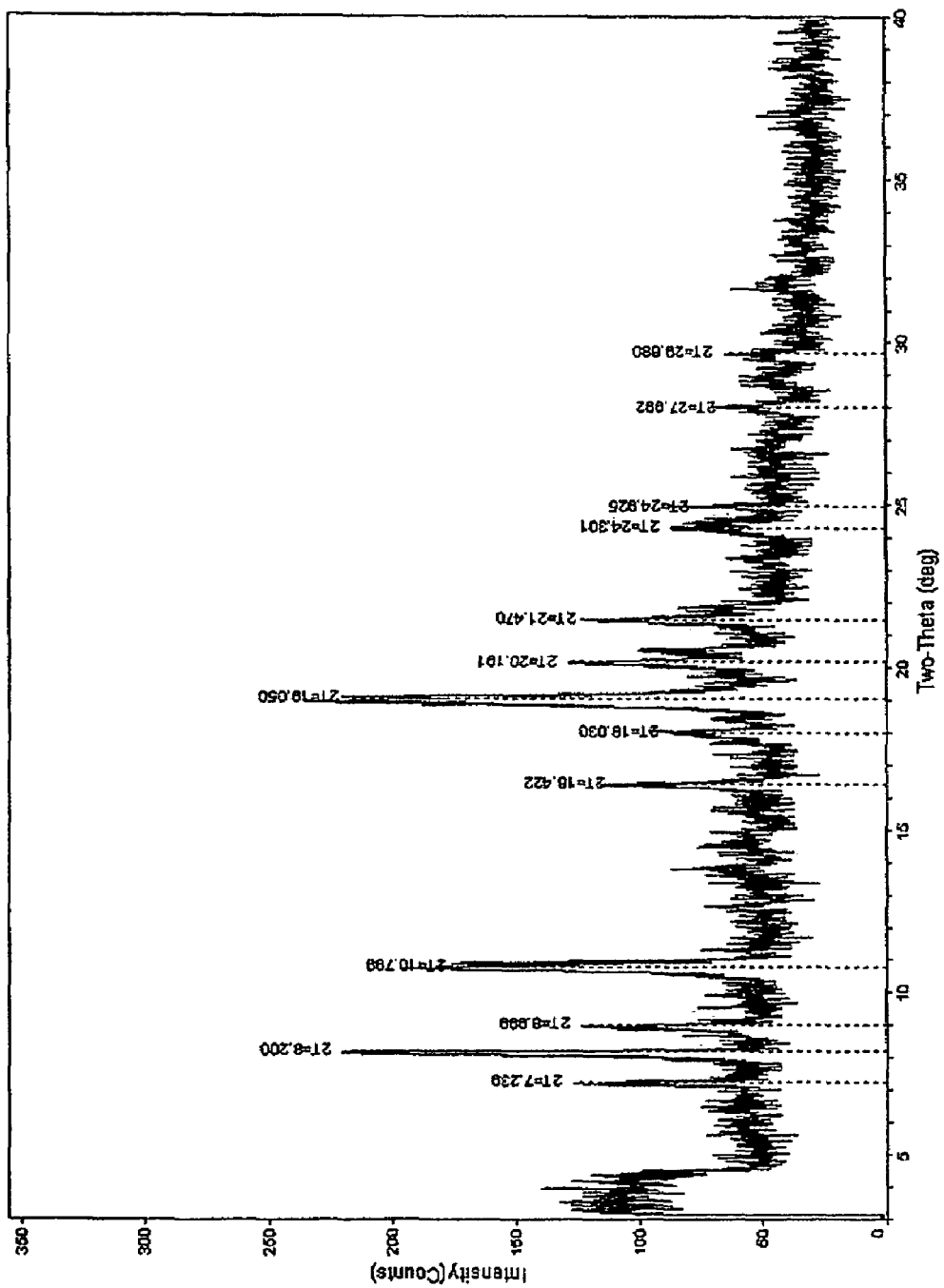
FIG. 1 depicts the X-ray powder diffraction pattern for compound 2.

General Description of Certain Aspects of the Invention

International patent application number PCT/EP/00/08190 (International publication number WO 01/14330) describes various indole-containing piperazine derivatives, including compound 1 (8-{4-[3-(5-fluoro-1H-indol-3-yl)-propyl]-piperazin-1-yl}-2-methyl-4H-benzo[1,4]oxazin-3-one, shown), which exhibit antagonistic activity at $D_2$ receptors and inhibitory activity against 5HT reuptake in therapeutic models.

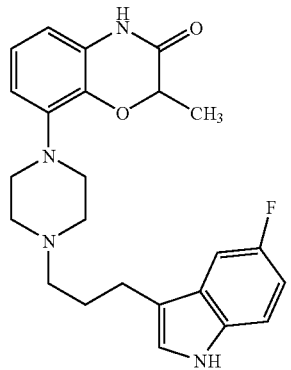

1

Additionally, compound 1 is active in therapeutic models which are sensitive to clinically relevant antipsychotics, antidepressants, and anxiolytics, as well as Parkinson's disease. Accordingly, compound 1 is useful for treating Parkinson's disease, psychoses (e.g., schizophrenia, mania, psychotic depression, and bipolar disorder), depression, stress/anxiety, panic disorder, Alzheimer's disease, obsessive compulsive disorder, eating disorders, drug addiction, social phobias, aggression or agitation, migraine, scleroderma and Raynaud's phenomenon, emesis, GI tract disorders related to the regulation of peristalsis, RLS, and to suppress prolactin secretion arising from tumours of the pituitary gland. Furthermore, compound 1 has a low propensity to induce catalepsy in rodents and is therefore less likely to induce extrapyramidal side effects than existing antipsychotics. See: WO 01/14330; van der Heyden and Bradford. Behav. Brain Res. 31:61 (1988); van der Poel et al. Psychopharmacology, 97:147 (1989); and Ungerstedt. Acta Physiol. Scand. 82: (suppl. 367) 69 (1971).

Non-steroidal anti-inflammatory drugs are known to inhibit prostaglandin synthesis and other related metabolic products of arachidonic acid via interference with cyclooxygenase (COX) enzymes. There is evidence that hyperactive COX activity is exhibited in the brains of schizophrenic patients, and thus abnormalities in the prostaglandin pathway are implicated in the pathogenesis of schizophrenia. Thus, without wishing to be bound by any particular theory, it is believed that the use of a salt formed from compound 1 with an acid capable of interfering with the production of prostaglandins, or interfering with the COX enzyme, would impart additional benefits and/or synergistic effects in the treatment of patients with schizophrenia and other psychotic disorders. See: Das and Khan. Prostaglandins Leukot Essent Fatty Acids 58:165 (1998).

In general, the present invention provides a salicylate or gentisate (2,5-dihydroxybenzoate) salt of compound 1.

In certain embodiments, the present invention provides a salicylate salt of compound 1, represented by compound 2:

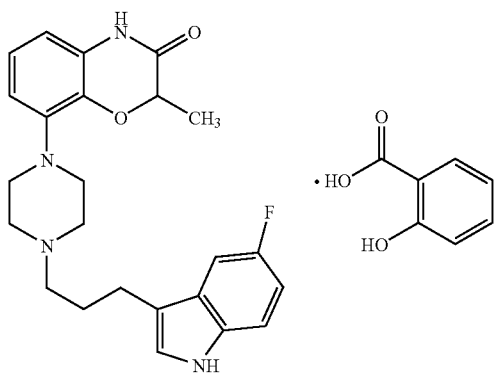

2

It will be appreciated by one of ordinary skill in the art that the salicylic acid and compound 1 are ionically bonded to form compound 2. It is contemplated that compound 2 can exist in a variety of physical forms. For example, compound 2 can be in solution, suspension, or in solid form. In certain embodiments, compound 2 is in solid form. When compound 2 is in solid form, said compound may be amorphous, crystalline, or mixtures thereof.

In certain embodiments, compound 2 is a crystalline solid. In other embodiments, compound 2 is a crystalline solid substantially free of amorphous compound 2. As used herein, the term "substantially free of amorphous compound 2" means that the compound contains no significant amount of amorphous compound 2. In certain embodiments, at least about 95% by weight of crystalline compound 2 is present. In still other embodiments of the invention, at least about 99% by weight of crystalline compound 2 is present. According to one aspect, compound 2 has a powder X-ray diffraction pattern substantially similar to that depicted in FIG. 1. According to another embodiment, compound 2 is crystalline and is characterized in that it has one or more peaks selected from those at about 8.2, 10.799, or 19.050 degrees 2-theta.

According to another embodiment, the present invention provides compound 2 as an amorphous solid. Amorphous solids are well known to one of ordinary skill in the art and are typically prepared by such methods as lyophilization, melting, and precipitation from supercritical fluid, among others.

In other embodiments, the present invention provides compound 2 substantially free of impurities. As used herein, the term "substantially free of impurities" means that the compound contains no significant amount of extraneous matter. Such extraneous matter may include excess salicylic acid, excess compound 1, residual solvents, or any other impurities that may result from the preparation of, and/or isolation of, compound 2. In certain embodiments, at least about 95% by weight of compound 2 is present. In still other embodiments of the invention, at least about 99% by weight of compound 2 is present.

According to one embodiment, compound 2 is present in an amount of at least about 97, 97.5, 98, 98.5, 99, 99.5, 99.8 weight percent where the percentages are based on the total weight of the composition. According to another embodiment, compound 2 contains no more than about 2.0 area percent HPLC of total organic impurities and, in certain embodiments, no more than about 1.5 area percent HPLC total organic impurities relative to the total area of the HPLC chromatogram. In other embodiments, compound 2 contains no more than about 0.6 area percent HPLC of any single impurity, and, in certain embodiments, no more than about 0.5 area percent HPLC of any single impurity, relative to the total area of the HPLC chromatogram.

The structure depicted for compound 2 is also meant to include all isomeric (e.g., enantiomeric or conformational) forms of the structure. For example, both the R and the S configurations at the stereogenic carbon are included in this invention. Therefore, single stereochemical isomers as well as enantiomeric and conformational mixtures of the present compound are within the scope of the invention. Furthermore, all tautomeric forms of compound 2 are within the scope of the present invention. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

In certain embodiments, the present invention provides a gentisate salt of compound 1, represented by compound 3:

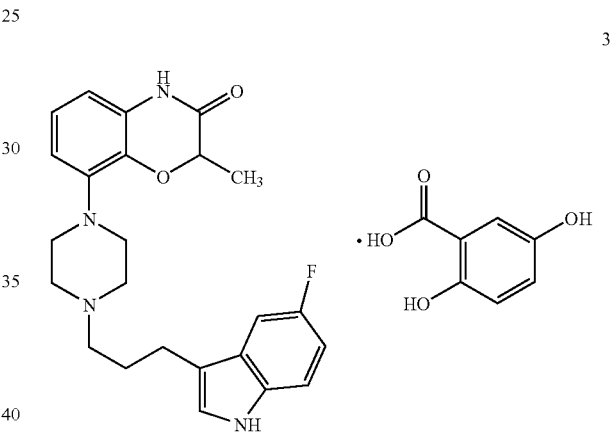

3

It will be appreciated by one of ordinary skill in the art that the gentisic acid and compound 1 are ionically bonded to form compound 3. It is contemplated that compound 3 can exist in a variety of physical forms. For example, compound 3 can be in solution, suspension, or in solid form. In certain embodiments, compound 3 is in solid form. When compound 3 is in solid form, said compound may be amorphous, crystalline, or mixtures thereof.

Figure 2A:
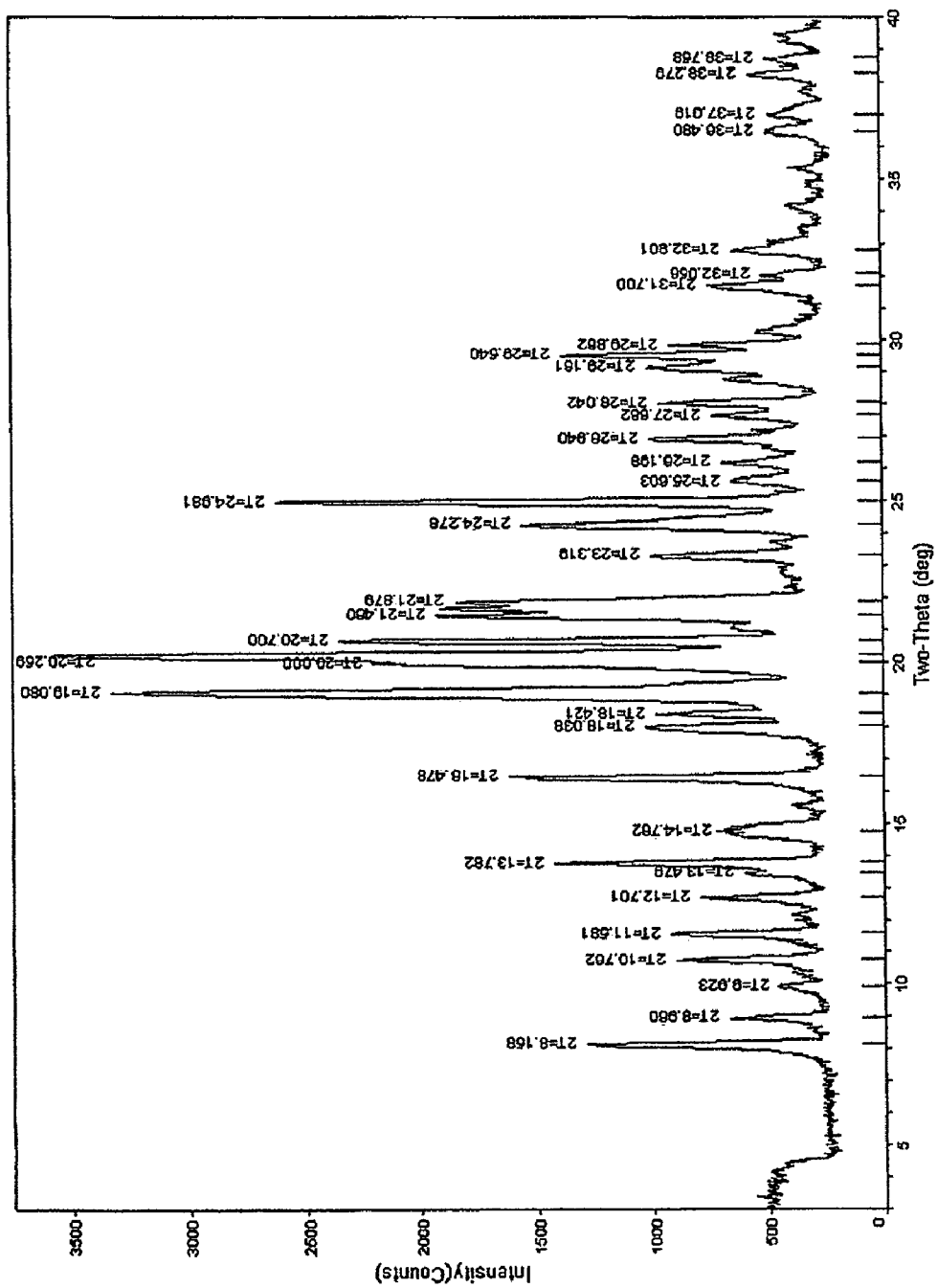
FIG. 2 depicts the X-ray powder diffraction pattern for compound 3.

In certain embodiments, compound 3 is a crystalline solid. In other embodiments, compound 3 is a crystalline solid substantially free of amorphous compound 3. As used herein, the term "substantially free of amorphous compound 3" means that the compound contains no significant amount of amorphous compound 3. In certain embodiments, at least about 95% by weight of crystalline compound 3 is present. In still other embodiments of the invention, at least about 99% by weight of crystalline compound 3 is present. According to one aspect, compound 3 has a powder X-ray diffraction pattern substantially similar to that depicted in FIG. 2. According to another embodiment, compound 3 is crystalline and is characterized in that it has one or more peaks selected from those at about 19.080, 20.259, or 24.981 degrees 2-theta.

According to another embodiment, the present invention provides compound 3 as an amorphous solid. Amorphous solids are well known to one of ordinary skill in the art and are typically prepared by such methods as lyophilization, melting, and precipitation from supercritical fluid, among others.

In other embodiments, the present invention provides compound 3 substantially free of impurities. As used herein, the term "substantially free of impurities" means that the compound contains no significant amount of extraneous matter. Such extraneous matter may include excess salicylic acid, excess compound 1, residual solvents, or any other impurities that may result from the preparation of, and/or isolation of, compound 3. In certain embodiments, at least about 95% by weight of compound 3 is present. In still other embodiments of the invention, at least about 99% by weight of compound 3 is present.

According to one embodiment, compound 3 is present in an amount of at least about 97, 97.5, 98, 98.5, 99, 99.5, 99.8 weight percent where the percentages are based on the total weight of the composition. According to another embodiment, compound 3 contains no more than about 2.0 area percent HPLC of total organic impurities and, in certain embodiments, no more than about 1.5 area percent HPLC total organic impurities relative to the total area of the HPLC chromatogram. In other embodiments, compound 3 contains no more than about 0.6 area percent HPLC of any single impurity, and, in certain embodiments, no more than about 0.5 area percent HPLC of any single impurity, relative to the total area of the HPLC chromatogram.

The structure depicted for compound 3 is also meant to include all isomeric (e.g., enantiomeric or conformational) forms of the structure. For example, both the R and the S configurations at the stereogenic carbon are included in this invention. Therefore, single stereochemical isomers as well as enantiomeric and conformational mixtures of the present compound are within the scope of the invention. Furthermore, all tautomeric forms of compound 3 are within the scope of the present invention. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}C$- or $^{14}C$-enriched carbon are within the scope of this invention.

General Methods of Providing the Present Compounds:

Compound 1 is prepared according to the methods described in detail in PCT publication number WO 01/14330, the entirety of which is hereby incorporated herein by reference.

Another aspect of the present invention provides a method for preparing compound 2:

comprising the steps of:

providing compound 1:

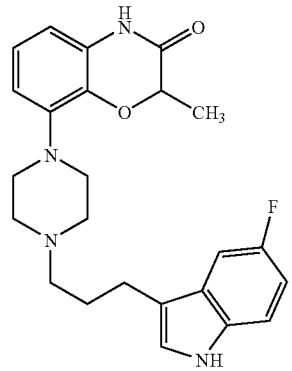

combining compound 1 with salicyclic acid in a suitable solvent; and optionally isolating compound 2.

A suitable solvent may solubilize one or more of the reaction components, or, alternatively, the suitable solvent may facilitate the agitation of a suspension of one or more of the reaction components. Examples of suitable solvents useful in the present invention are a protic solvent, a polar aprotic solvent, or mixtures thereof. In certain embodiments, suitable solvents include an ether, an ester, an alcohol, a ketone, or mixtures thereof. In certain embodiments, the suitable solvent is methanol, ethanol, isopropanol, or acetone wherein said solvent is anhydrous or in combination with water or heptane. In other embodiments, suitable solvents include tetrahydrofuran, dimethylformamide, dimethylsulfoxide, glyme, diglyme, methyl t-butyl ether, t-butanol, n-butanol, and acetonitrile. In another embodiment, the suitable solvent is anhydrous ethanol.

According to another embodiment, the present invention provides a method for preparing compound 2:

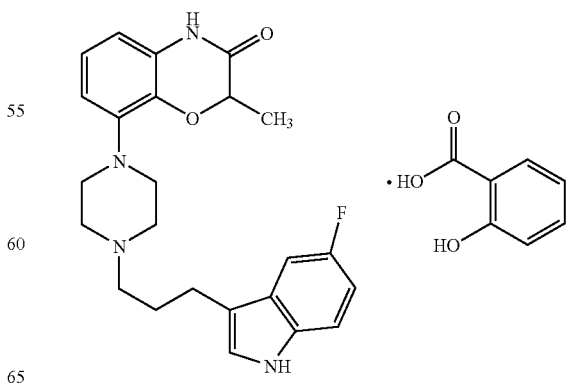

comprising the steps of:
combining compound 1:

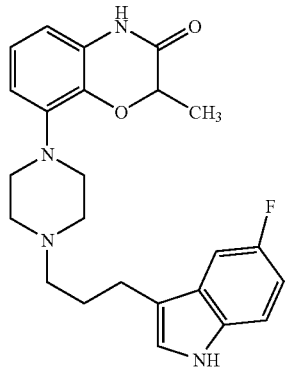

with a suitable solvent and heating to form a solution thereof;
adding salicylic acid to said solution; and
optionally isolating compound 2.

In certain embodiments, compound 1 is dissolved in a suitable solvent with heating. In certain embodiments compound 1 is dissolved at about 60° C. In other embodiments, compound 1 is dissolved in a suitable solvent at about 40° C. In yet other embodiments, compound 1 is dissolved at a temperature between about 40° C. and about 60° C. In still other embodiments, compound 1 is dissolved in a suitable solvent at the reflux temperature of the suitable solvent. In other embodiments, compound 1 is dissolved in a suitable solvent without heating.

In certain embodiments, the solution of compound 1 is filtered prior to the addition of salicylic acid. In other embodiments, the solution of compound 1 is not filtered prior to the addition of salicylic acid.

In certain embodiments, where the solution of compound 1 was heated to any temperature between about 40° C. and about 60° C., the solution is subsequently cooled to any lower temperature that is between about 20° C. and about 40° C. prior to the addition of salicylic acid. In other embodiments, where the solution of compound 1 was heated to any temperature between about 40° C. and about 60° C., the solution is not subsequently cooled to any lower temperature prior to the addition of salicylic acid.

In certain embodiments, about 1 equivalent of salicylic acid is added to compound 1 to afford compound 2. In other embodiments, less than 1 equivalent of salicylic acid is added to compound 1 to afford compound 2. In yet other embodiments, greater than 1 equivalent of salicylic acid is added to compound 1 to afford compound 2. In other embodiments, about 1.0 to about 1.2 equivalents of salicylic acid is added to compound 1 to afford compound 2. In still other embodiments, about 0.9 to about 1.1 equivalents of salicylic acid is added to compound 1 to afford compound 2. In another embodiment, about 0.99 to about 1.01 equivalents of salicylic acid is added to compound 1 to afford compound 2.

It will be appreciated that the salicylic acid may be added to the mixture of compound 1 and a suitable solvent in any suitable form. For example, the salicylic acid may be added in solid form or as a solution or a suspension in a suitable solvent. The suitable solvent may be the same suitable solvent as that which is combined with compound 1 or may be a different solvent. In certain embodiments, the salicylic acid combined with a suitable solvent prior to adding to compound 1. According to another embodiment, the salicylic acid is added as a solution in a suitable solvent. In other embodiments, the suitable solvent in which salicylic acid is dissolved is a polar protic or polar aprotic solvent. Such solvents include alcohols, ethers, and ketones. Examples of such solvents include methanol, ethanol, isopropanol, acetone, tetrahydrofuran, dimethylformamide, dimethylsulfoxide, glyme, diglyme, methyl t-butyl ether, t-butanol, n-butanol, and acetonitrile. In certain embodiments the suitable solvent is selected from those above and is anhydrous. In other embodiments, the suitable solvent is selected from those above and is a mixture with water or heptane. In another embodiment, the suitable solvent is anhydrous ethanol.

In certain embodiments, the resulting mixture containing compound 2 is cooled. In certain embodiments where the mixture containing compound 2 is heated above about 20° C., the solution is allowed to cool to about 20° C. In other embodiments, the mixture containing compound 2 is cooled below 20° C. In certain embodiments, the mixture containing compound 2 is cooled to between about −15° C. and about 0° C. prior to adding to compound 1.

In certain embodiments, compound 2 precipitates from the mixture. In another embodiment, compound 2 crystallizes from the mixture. In other embodiments, compound 2 crystallizes from solution following seeding of the solution (i.e., adding crystals of compound 2 to the solution). In still other embodiments, compound 2 crystallizes from solution onto a glass frit that is submerged in the solution. In yet other embodiments, compound 2 crystallizes from solution following cycles wherein the headspace pressure above the solution is varied between about 400 torr and about 760 torr. In certain embodiments, compound 2 crystallizes with agitation (e.g., stirring). In other embodiments, compound 2 crystallizes without agitation. In certain embodiments, compound 2 crystallizes from solution upon the addition of a suitable miscible anti-solvent. In another embodiment, the suitable miscible anti-solvent is heptane.

As described generally above, compound 2 is optionally isolated. It will be appreciated that compound 2 may be isolated by any suitable physical means known to one of ordinary skill in the art. In certain embodiments, precipitated solid compound 2 is separated from the supernatant by filtration. In other embodiments, precipitated solid compound 2 is separated from the supernatant by decanting the supernatant.

In still other embodiments, isolated s compound 2 is optionally rinsed with a suitable solvent. In certain embodiments this solvent is methanol, ethanol, propanol, butanol, or t-butanol. In other embodiments, isolated compound 2 is not rinsed following removal of the supernatant.

In certain embodiments, isolated compound 2 is dried in air at ambient pressure. In other embodiments isolated compound 2 is dried under reduced pressure. In certain embodiments, isolated compound 2 is dried under reduced pressure wherein the pressure is between about 0.05 torr and about 50 torr. In a preferred embodiment, isolated compound 2 is dried under reduced pressure wherein the pressure is about 25 torr.

In another aspect of the present invention, compound 2 is not isolated from the mixture.

In other embodiments, in the resulting compound 3, the ratio of salicylic acid to compound 1 obtained is between about 0.8 and about 2.0. In certain embodiments, the ratio is between about 0.9 and about 1.2. In other embodiments, the ratio is between about 0.94 and about 1.06.

Another aspect of the present invention provides a method for preparing compound 3:

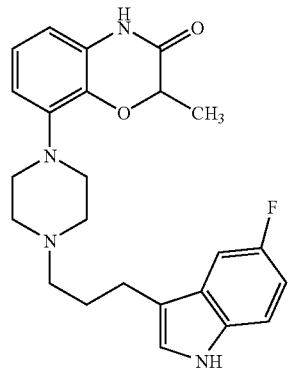 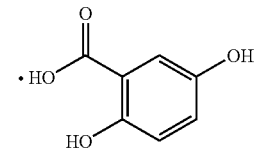 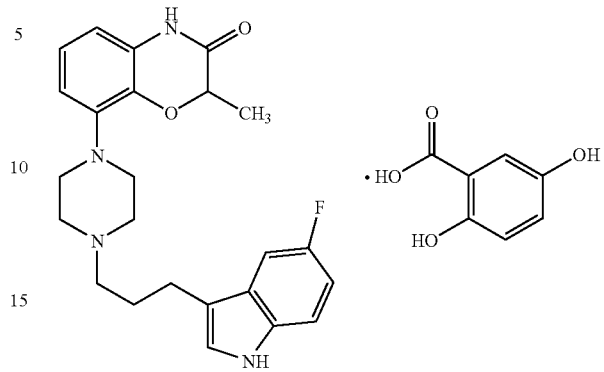

comprising the steps of:
providing compound 1:

comprising the steps of:
combining compound 1:

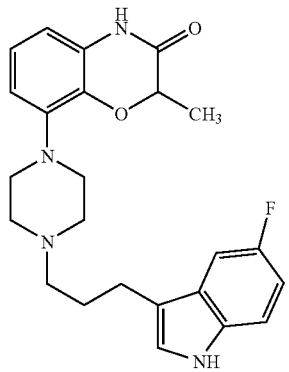

combining compound 1 with gentisic acid in a suitable solvent; and optionally isolating compound 3.

A suitable solvent may solubilize one or more of the reaction components, or, alternatively, the suitable solvent may facilitate the agitation of a suspension of one or more of the reaction components. Examples of suitable solvents useful in the present invention are a protic solvent, a polar aprotic solvent, or mixtures thereof. In certain embodiments, suitable solvents include an ether, an ester, an alcohol, a ketone, or mixtures thereof. In certain embodiments, the suitable solvent is methanol, ethanol, isopropanol, or acetone wherein said solvent is anhydrous or in combination with water or heptane. In other embodiments, suitable solvents include tetrahydrofuran, dimethylformamide, dimethylsulfoxide, glyme, diglymre, methyl t-butyl ether, t-butanol, n-butanol, and acetonitrile. In another embodiment, the suitable solvent is anhydrous ethanol.

According to another embodiment, the present invention provides a method for preparing compound 3:

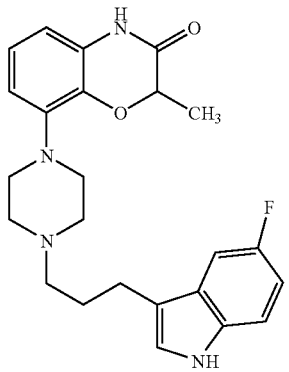

with a suitable solvent and heating to form a solution thereof;

adding gentisic acid to said solution; and optionally isolating compound 3.

In certain embodiments, compound 1 is dissolved in a suitable solvent with heating. In certain embodiments compound 1 is dissolved at about 60° C. In other embodiments, compound 1 is dissolved in a suitable solvent at about 40° C. In yet other embodiments, compound 1 is dissolved at a temperature between about 40° C. and about 60° C. In still other embodiments, compound 1 is dissolved in a suitable solvent at the reflux temperature of the suitable solvent. In other embodiments, compound 1 is dissolved in a suitable solvent without heating.

In certain embodiments, the solution of compound 1 is filtered prior to the addition of gentisic acid. In other embodiments, the solution of compound 1 is not filtered prior to the addition of gentisic acid.

In certain embodiments, where the solution of compound 1 was heated to any temperature between about 40° C. and about 60° C. the solution is subsequently cooled to any lower temperature that is between about 20° C. and about 40° C. prior to the addition of gentisic acid. In other embodiments, where the solution of compound 1 was heated to any temperature between about 40° C. and about 60° C., the solution is not subsequently cooled to any lower temperature prior to the addition of gentisic acid.

In certain embodiments, about 1 equivalent of gentisic acid is added to compound 1 to afford compound 3. In other embodiments, less than 1 equivalent of gentisic acid is added to compound 1 to afford compound 3. In yet other embodiments, greater than 1 equivalent of gentisic acid is added to compound 1 to afford compound 3. In other embodiments, about 1.0 to about 1.2 equivalents of gentisic acid is added to compound 1 to afford compound 3. In still other embodiments, about 0.9 to about 1.1 equivalents of gentisic acid is added to compound 1 to afford compound 3. In another embodiment, about 0.99 to about 1.01 equivalents of gentisic acid is added to compound 1 to afford compound 3.

It will be appreciated that the gentisic acid may be added to the mixture of compound 1 and a suitable solvent in any suitable form. For example, the gentisic acid may be added in solid form or as a solution or a suspension in a suitable solvent. The suitable solvent may be the same suitable solvent as that which is combined with compound 1 or may be a different solvent. In certain embodiments, the gentisic acid combined with a suitable solvent prior to adding to compound 1. According to another embodiment, the gentisic acid is added as a solution in a suitable solvent. In other embodiments, the suitable solvent in which gentisic acid is dissolved is a polar protic or polar aprotic solvent. Such solvents include alcohols, ethers, and ketones. Examples of such solvents include methanol, ethanol, isopropanol, acetone, tetrahydrofuran, dimethylformamide, dimethylsulfoxide, glyme, diglyme, methyl t-butyl ether, t-butanol, n-butanol, and acetonitrile. In certain embodiments the suitable solvent is selected from those above and is anhydrous. In other embodiments, the suitable solvent is selected from those above and is a mixture with water or heptane. In another embodiment, the suitable solvent is anhydrous ethanol.

In certain embodiments, the resulting mixture containing compound 3 is cooled. In certain embodiments where the mixture containing compound 3 is heated above about 20° C., the solution is allowed to cool to about 20° C. In other embodiments, the mixture containing compound 3 is cooled below 20° C. In certain embodiments, the mixture containing compound 3 is cooled to between about −15° C. and about 0° C. prior to adding to compound 1.

In certain embodiments, compound 3 precipitates from the mixture. In another embodiment, compound 3 crystallizes from the mixture. In other embodiments, compound 3 crystallizes from solution following seeding of the solution (i.e., adding crystals of compound 3 to the solution). In still other embodiments, compound 3 crystallizes from solution onto a glass frit that is submerged in the solution. In yet other embodiments, compound 3 crystallizes from solution following cycles wherein the headspace pressure above the solution is varied between about 400 torr and about 760 torr. In certain embodiments, compound 3 crystallizes with agitation (e.g., stirring). In other embodiments, compound 3 crystallizes without agitation. In certain embodiments, compound 3 crystallizes from solution upon the addition of a suitable miscible anti-solvent. In another embodiment, the suitable miscible anti-solvent is heptane.

As described generally above, compound 3 is optionally isolated. It will be appreciated that compound 3 may be isolated by any suitable physical means known to one of ordinary skill in the art. In certain embodiments, precipitated solid compound 3 is separated from the supernatant by filtration. In other embodiments, precipitated solid compound 3 is separated from the supernatant by decanting the supernatant.

In still other embodiments, isolated s compound 3 is optionally rinsed with a suitable solvent. In certain embodiments this solvent is methanol, ethanol, propanol, butanol, or t-butanol. In other embodiments, isolated compound 3 is not rinsed following removal of the supernatant.

In certain embodiments, isolated compound 3 is dried in air at ambient pressure. In other embodiments isolated compound 3 is dried under reduced pressure. In certain embodiments, isolated compound 3 is dried under reduced pressure wherein the pressure is between about 0.05 torr and about 50 torr. In another, isolated compound 3 is dried under reduced pressure wherein the pressure is about 25 torr.

In another aspect of the present invention, compound 3 is not isolated from the mixture.

In other embodiments, in the resulting compound 3, the ratio of gentisic acid to compound 1 obtained is between about 0.8 and about 2.0. In certain embodiments, the ratio is between about 0.9 and about 1.2. In other embodiments, the ratio is between about 0.94 and about 1.06.

Uses of Compounds and Pharmaceutically Acceptable Compositions

As discussed above, the present invention provides compounds that are useful as modulators of D receptors, 5HT receptors, 5HT reuptake, and prostaglandin synthesis, and show utility in clinically relevant models for psychoses, depression, stress/anxiety, and Parkinson's disease. In certain embodiments, the present salts are useful as modulators of one or more of $D_2$ receptor subtype, 5HT reuptake, or prostaglandin synthesis. In other embodiments, the present compounds are useful for the treatment of psychoses, depression, stress/anxiety, and Parkinson's disease.

Accordingly, in another aspect of the present invention, pharmaceutically acceptable compositions are provided, wherein these compositions comprise compound 2, compound 3, or mixtures thereof, and optionally a pharmaceutically acceptable carrier, adjuvant, or vehicle. In certain embodiments, these compositions optionally further comprise one or more additional therapeutic agents.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the salts of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, a method for treating or lessening the severity of a disorder associated with the modulation of D receptors, 5HT receptors, 5HT reuptake, and prostaglandin synthesis, and/or for treating or lessening the severity of psychoses, depression, stress/anxiety, and/or Parkinson's disease is provided, comprising administering an effective amount of compound 2, compound 3, or mixtures thereof, to a subject in need thereof. In certain embodiments of the present invention an "effective amount" of the compound or pharmaceutically acceptable composition is that amount effective for treating or lessening the severity of a disorder associated with the modulation of D receptors, 5HT receptors, 5HT reuptake, and prostaglandin synthesis, and/or for treating or lessening the severity of psychoses, depression, stress/anxiety, and/or Parkinson's disease. In other embodiments, an "effective amount" of a compound is an amount which acts as a modulator of one or more of D receptors, 5HT receptors, 5HT reuptake, and prostaglandin synthesis. An "effective amount" of a compound can achieve a desired therapeutic and/or prophylactic effect, such as an amount which results in the prevention of, or a decrease in the symptoms associated with, a disease associated with one or more of D receptor, 5HT receptor, 5HT reuptake, and prostaglandin synthesis modulation, and/or with psychoses, depression, stress/anxiety, and/or Parkinson's disease.

The compounds and compositions, according to the methods of the present invention, may be administered using any amount and any route of administration effective for treating or lessening the severity of a disorder associated with modulation of one or more of D receptors, 5HT receptors, 5HT reuptake, and prostaglandin synthesis, and/or for treating or lessening the severity of psychoses, depression, stress/anxiety, and/or Parkinson's disease. The exact amount required will vary from subject to subject, depending on the species, age, and general condition of the subject, the severity of the infection, the particular agent, its mode of administration, and the like. The compounds of the invention are preferably formulated in dosage unit form (e.g., as a tablet, capsule, or ampoule) for ease of administration and uniformity of dosage. The expression "dosage unit form" as used herein refers to a physically discrete unit of agent appropriate for the patient to be treated. It will be understood, however, that the total daily usage of the salts and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, nasally, rectally, parenterally, intracisternally, intravaginally, intraperitoneally, topically (as by powders, ointments, or drops), bucally, or the like, depending on the severity of the infection being treated. In certain embodiments, the salts of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral or nasal administration include, but are not limited to, pharmaceutically acceptable emulsions, microemulsions, solutions, suspensions, aerosols, gels, syrups, and elixirs. In addition to the active salts, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a pharmaceutically acceptable propellant. The aerosol dosage forms can also take the form of a pump-atomiser.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection.

This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Typical parenteral compositions consist of a solution or suspension of the compound or physiologically acceptable salt in a sterile aqueous carrier or non-aqueous or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for rectal or vaginal administration are conveniently in the form of suppositories, pessaries, vaginal tabs, foams, or enemas. Compositions for rectal or vaginal administration are preferably suppositories which can be prepared by mixing the salts of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium salts, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Compositions suitable for buccal or sublingual administration include tablets, lozenges and pastilles, wherein the active ingredient is formulated with a carrier such as sugar and acacia, tragacanth, or gelatin and glycerin.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active salts can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Compositions for oral administration may be designed to protect the active ingredient against degradation as it passes through the alimentary tract, for example by an outer coating of the formulation on a tablet or capsule.

Compound 2 and compound 3, according to the present invention, can be provided in a delayed release composition. This delayed release composition comprises compound 2 and/or compound 3 in combination with a delayed release component. This composition allows targeted release of compound 2 and/or compound 3 into the lower gastrointestinal tract; for example into the small intestine, the large intestine, the colon and/or the rectum. The delayed release composition may comprise compound 2 and/or compound 3 and an enteric or pH dependent coating such as cellulose acetate phthalates and other phthalates (e.g. polyvinyl acetate phthalate, methacrylates (Eudragits)). Alternatively, the delayed release composition may provide controlled release to the small intestine and/or colon by the provision of pH sensitive methacrylate coatings, pH sensitive polymeric microspheres, or polymers which undergo degradation by hydrolysis. The delayed release composition can be formulated with hydrophobic or gelling excipients or coatings. Colonic delivery can further be provided by coatings which are digested by bacterial enzymes such as amylose or pectin, by pH dependent polymers, by hydrogel plugs swelling with time (Pulsincap), by time dependent hydrogel coatings and/or by acrylic acid linked to azoaromatic bonds coatings.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions may contain from 0.1% to 99% (w/w) preferably from 0.1-60% (w/w), more preferably 0.2-20% by weight and most preferably 0.25 to 12% (w/w) of the compound 2 and/or compound 3, depending on the method of administration.

As described generally above, the salts of the present invention are useful as modulators of one or more of D receptors, 5HT receptors, 5HT reuptake, and prostaglandin synthesis and thus the invention further relates to a method for treating (e.g., palliative, curative, prophylactic) a disease or disorder associated with modulation of one or more of D receptors, 5HT receptors, 5HT reuptake, and prostaglandin synthesis.

In one embodiment, the salts and compositions of the invention are modulators of one or more of D receptors, 5HT receptors, 5HT reuptake, and prostaglandin synthesis, and thus, without wishing to be bound by any particular theory, the salts and compositions are particularly useful for treating or lessening the severity of a disease, condition, or disorder where modulation of one or more of D receptors, 5HT receptors, 5HT reuptake, and prostaglandin synthesis is implicated in the disease, condition, or disorder. When modulation of one or more of D receptors, 5HT receptors, 5HT reuptake, and prostaglandin synthesis is implicated in a particular disease, condition, or disorder, the disease, condition, or disorder may also be referred to as a "D receptor, 5HT receptor, 5HT reuptake, or prostaglandin synthesis-mediated disease" or disease symptom.

In certain embodiments, the salts and compositions of the present invention provide a method for treating or lessening the severity of one or more disorders including, but not limited to, Parkinson's disease, psychoses (e.g., schizophrenia, mania, psychotic depression, and bipolar disorder), depression, stress/anxiety, Alzheimer's disease, Huntington's disease, panic disorder, obsessive compulsive disorder, eating disorders, drug addiction, social phobias, aggression or agitation, migraine, scleroderma and Raynaud's phenomenon, emesis, GI tract disorders related to the regulation of peristalsis, RLS, and prolactin secretion arising from tumours of the pituitary gland, wherein said method comprises administering to a patient compound 2 and/or compound 3, or compositions thereof.

It will also be appreciated that the compounds and pharmaceutically acceptable compositions of the present invention can be employed in combination therapies, that is, the salts and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents which are normally administered to treat or prevent a particular disease, or condition, are known as "appropriate for the disease, or condition, being treated".

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Another aspect of the invention relates to modulating D receptors, 5HT receptors, 5HT reuptake, and prostaglandin synthesis activity in a biological sample or a patient, which method comprises administering to the patient, or contacting said biological sample with compound 2 and/or compound 3, or a composition thereof. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of D receptors, 5HT receptors, 5HT reuptake, and prostaglandin synthesis activity in a biological sample is useful for a variety of purposes that are known to one of skill in the art. Examples of such purposes include, but are not limited to, biological assays.

The amount of compound 2 and/or compound 3 effective to treat a disorder as set out above depends on the nature and severity of the disorder being treated and the weight of the patient in need thereof. However, a single unit dose for a 70 kg adult will normally contain 0.01 to 100 mg, for example 0.1 to 50 mg, preferably 0.5 to 16 mg of the compound of the invention per day. Unit doses may be administered once or more than once a day, for example, 2, 3 or 4 times a day, usually 1 to 3 times a day, more preferably 1 or 2 times per day. It will be appreciated that the dose ranges set out above provided guidance for the administration of compound 2 and/or compound 3 to an adult. The amount to be administered to for example, an infant or a baby can be determined by a medical practitioner or person skilled in the art and can be lower or the same as that administered to an adult. The unit dose is preferably provided in the form of a capsule or a tablet.

All preferred features of each of the aspects of the invention apply to all other aspects mutatis mutandis.

In order that the invention described herein may be more fully understood, the following examples are set forth. It should be understood that these examples are for illustrative purposes only and are not to be construed as limiting this invention in any manner.

EXAMPLES

General Procedures

Powder X-ray diffraction patterns were obtained on a Rigaku Miniflex Diffraction System (Rigaku MSC Inc.). The powder samples were deposited on a zero-background polished silicon sample holder. A normal focus copper X-ray tube at 0.45 kW equipped with a Ni Kβ filter scanning at 2 degrees/minute from 3.00 to 40.00 degree 2-theta was used as the X-ray source. The data processing was done using Jade 6.0 software.

Proton Nuclear Magnetic Resonance ($^1$H NMR) spectra were obtained on a Bruker model Avance DRX-500 MHz NMR spectrometer, equipped with a 5 mm QNP probe. About 5-25 mg salts were dissolved in 0.6 mL DMSO-d6 (99.9% D), containing 0.05% TMS as an internal reference. $^1$H NMR spectra were recorded at 500.133 MHz, using a 30 degree pulse, with a pulse delay of 20 seconds, 32 k data points, 64 scans. An exponential window function with 0.3 Hz line broadening was applied to 16 k data points to process data without zero-filling and TMS was referred as 0.00 ppm.

Preparation of Compound 2

Method A

Compound 1 (50 mg) was slurried in anhydrous ethanol (4 mL) and heated to 40° C. to obtain a clear solution. To this solution, 16.3 mg of salicylic acid (0.99 equiv) was added. The resulting solution was cooled to 20° C. and stirred with a magnetic stirrer. A glass frit was introduced into the reactor and the headspace pressure above the solution was cycled between 760 torr and about 400 torr for 16 hours. This procedure yielded 2 phases: an oil phase in contact with the glass reactor and a solid phase on the glass frit. The solid on the glass frit was dried in air at 23° C. and analyzed by X-ray diffraction (FIG. 1) and found to be crystalline compound 2.

Table 1 below sets out the X-ray diffraction peaks observed for compound 2 wherein each value is in degrees 2-theta.

TABLE 1

X-ray Diffraction Peaks for Compound 2

| 2-Theta |
| --- |
| 7.239 |
| 8.2 |
| 8.999 |
| 10.799 |
| 16.422 |
| 18.03 |
| 19.05 |
| 20.191 |
| 21.47 |
| 24.301 |
| 24.925 |
| 27.992 |
| 29.68 |

Method B

Figure 3:
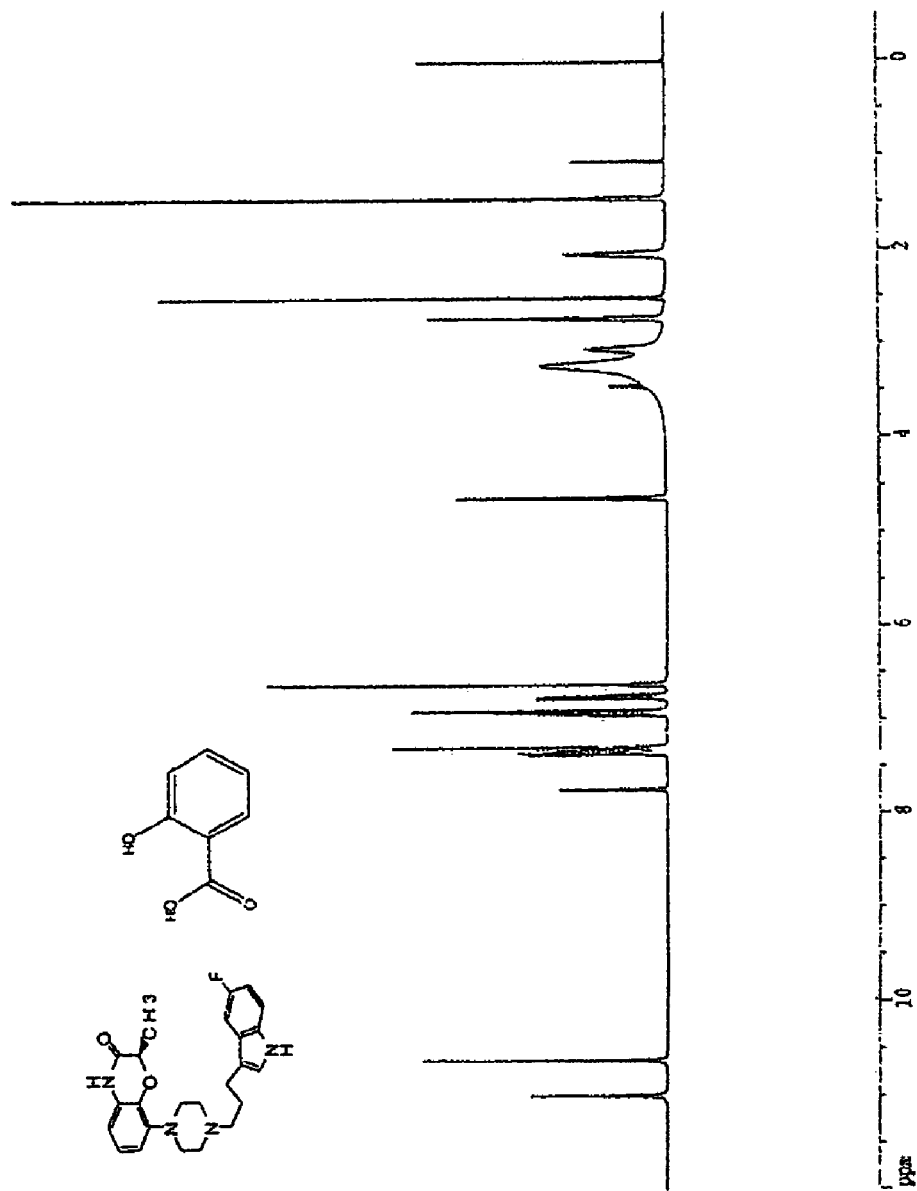
FIG. 3 depicts the $^1H$ NMR spectrum of compound 2 obtained at 500 MHz in DMSO-d6.

Alternatively, compound 2 was prepared in the following manner: compound 1 (500 mg) was slurried in 16 mL of anhydrous ethanol and heated to 60° C. to obtain a clear solution. The solution was filtered through a 0.45 μm filter and cooled to 40° C. To this solution, 164 mg of salicylic acid (1.0 equiv) as a solution in 4 mL ethanol was added. Solid seeds (1 mg) of 2 were added and the slurry was stirred at a temperature between about 20° C. and about 40° C. for 24 hours. The slurry was then filtered and the solid phase was dried at 25° C. and about 25 torr. The dry solid (372 mg, 56.1% yield) was characterized by X-ray diffraction and $^1$H NMR spectroscopy (FIG. 3) and found to be crystalline compound 2.

Preparation of Gentisate Salt 3

Method A

Compound 1 (50 mg) was slurried in anhydrous ethanol (4 mL) and heated to 40° C. to obtain a clear solution. To this solution, 18.2 mg of gentisic acid (1.0 equiv) was added. The resulting solution was cooled to 20° C. and stirred with a magnetic stirrer. A glass frit was introduced into the reactor and the headspace pressure above the solution was cycled between 760 torr and about 400 torr for 16 hours. This procedure yielded 2 solid phases: one in the glass reactor and a second on the glass frit. The solid on the glass frit was dried in air at 23° C. and analyzed by X-ray diffraction (FIG. 2) and found to be crystalline compound 3.

Table 2 below sets out the X-ray diffraction peaks observed for compound 3 wherein each value is in degrees 2-theta.

TABLE 2

X-ray Diffraction Peaks for Compound 3

| 2-Theta |
| --- |
| 8.158 |
| 8.96 |
| 9.923 |
| 10.762 |
| 11.581 |
| 12.701 |
| 13.479 |
| 13.782 |
| 14.762 |
| 16.478 |
| 18.038 |
| 18.421 |
| 19.08 |
| 20 |
| 20.259 |
| 20.7 |
| 21.46 |
| 21.879 |
| 23.319 |
| 24.278 |
| 24.981 |
| 25.603 |
| 26.198 |
| 26.94 |
| 27.662 |
| 28.042 |
| 29.161 |
| 29.54 |
| 29.862 |
| 31.7 |
| 32.056 |
| 32.801 |
| 36.48 |
| 37.019 |
| 38.279 |
| 38.758 |

Method B

Figure 4:
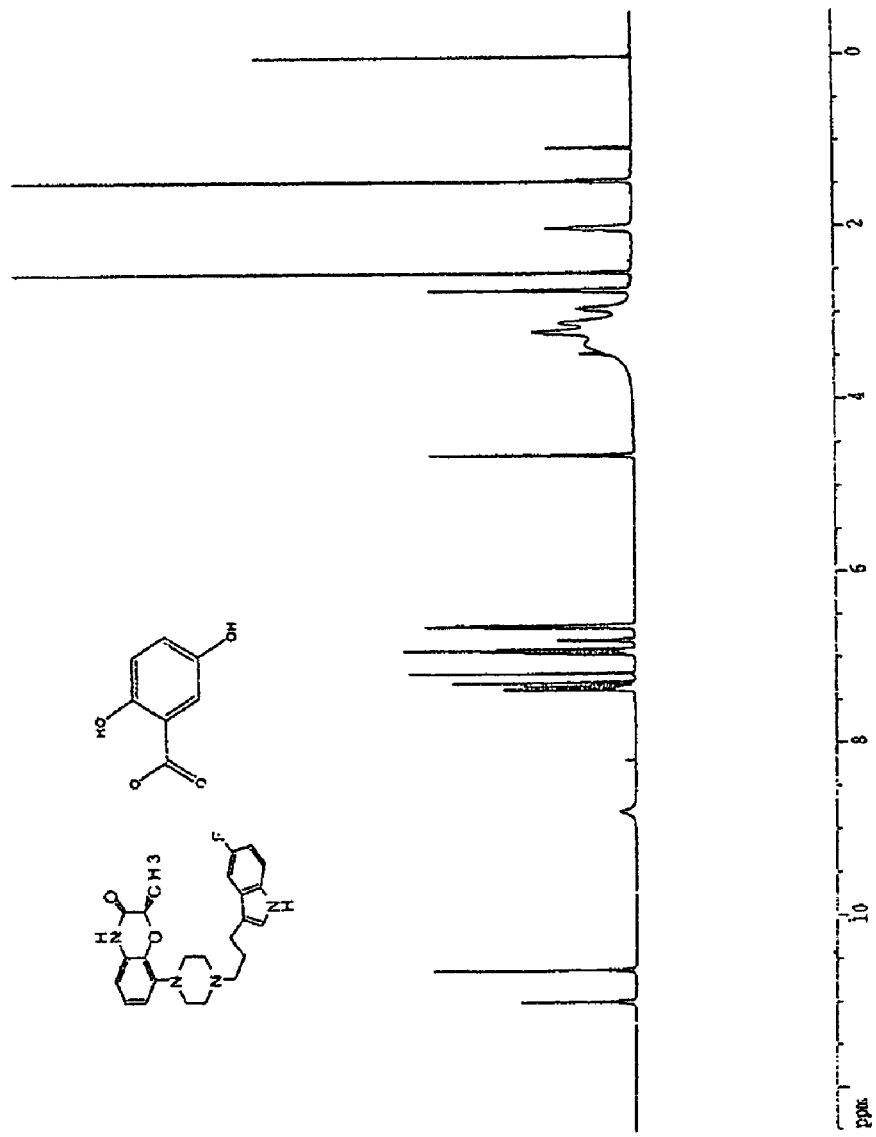
FIG. 4 depicts the $^1H$ NMR spectrum of compound 3 obtained at 500 MHz in DMSO-d6.

Alternatively, gentisate salt 3 was prepared in the following manner: compound 1 (500 mg) was slurried in 16 mL of anhydrous ethanol and heated to 60° C. to obtain a clear solution. The solution was filtered through a 0.45 μm filter and cooled to 40° C. To this solution, 182 mg of gentisic acid (1.0 equiv) as a solution in 4 mL ethanol was added and the solution was stirred at a temperature between about 20° C. and about 40° C. for 16 hours. During this period, a solid phase crystallized out. The slurry was then filtered and the solid phase was dried at 25° C. and about 25 torr. The dry solid (355 mg, 52.0% yield) was characterized by X-ray diffraction and NMR spectroscopy (FIG. 4) and found to be crystalline compound 3.

Water Solubility

Water solubility was determined by combining an excess amount of solid salt with ~2 mL $D_1$ water in a 4 mL glass screw-cap vial and equilibrating for at least 24 hours on an end-over-end rotator. The resulting suspensions were filtered through a 0.22 μm PVDF filter and assayed by high pressure liquid chromatography with quantitation by UV against standards of compound 1. The water solubility of compound 2 is 1.6 mg/mL (freebase equivalent) at a resulting pH of 5.8, while the solubility of the compound 3 is 0.5 mg/mL (freebase equivalent), also at pH 5.8.

NMR Results

Figure 5:
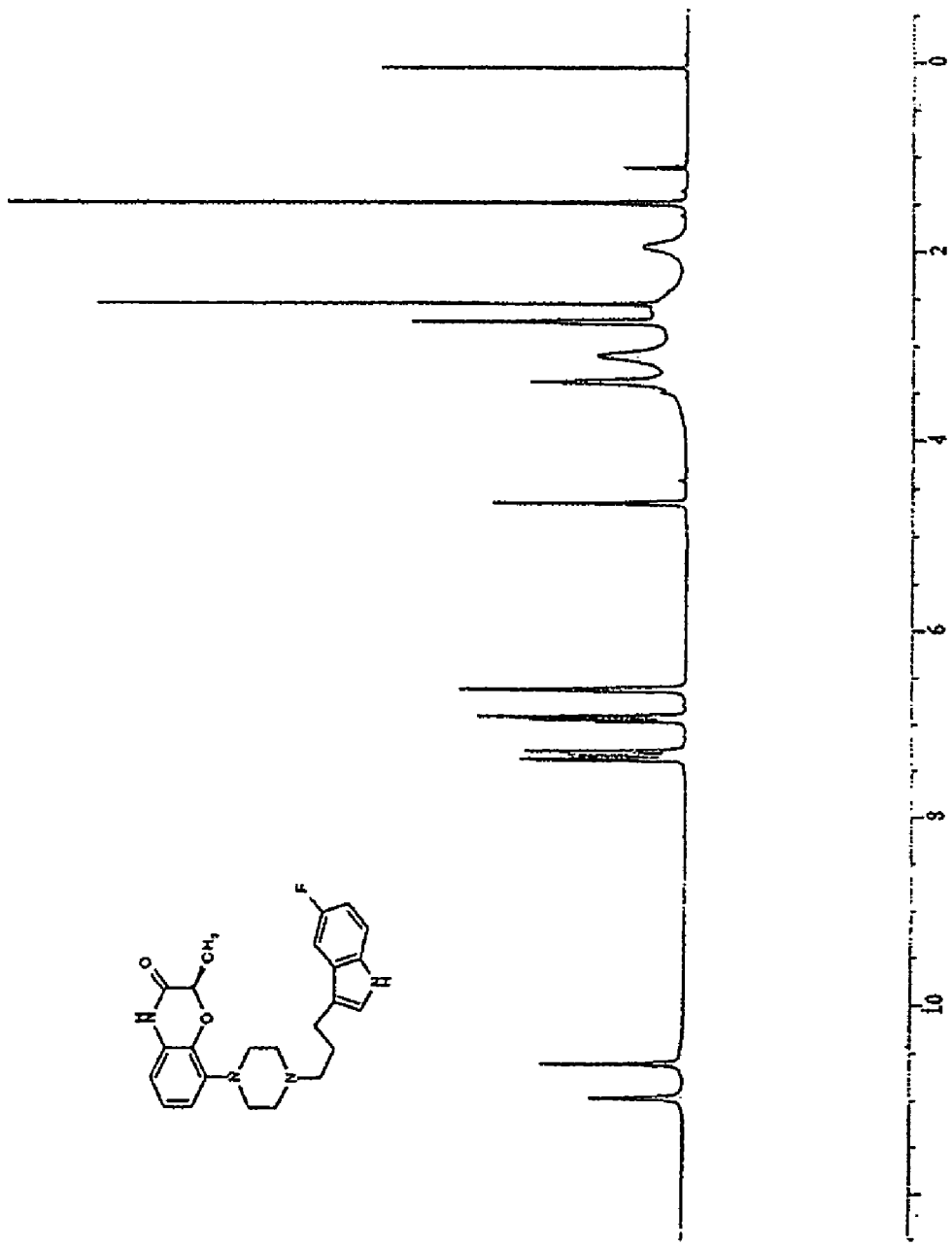
FIG. 5 depicts the $^1H$ NMR spectrum of compound 1 obtained at 500 MHz in DMSO-d6.

Integration of signals from salicylic acid and gentisic acid were compared with the unique peak of compound 1 (FIG. 5)

to obtain molar ratios of each acid to compound 1 in compound 2 and compound 3. The results are summarized in Table 1, below.

TABLE 1

| Counter Ion | Molar Ratio | Wt % Counter Ion | M.W. |
|---|---|---|---|
| Compound 1 (free base) | — | — | 422.5 |
| Salicylic Acid | 0.7 | 18.8 | 138.1 |
| Gentisic Acid | 0.8 | 21.6 | 154.1 |

We claim:

1. Compound 2:

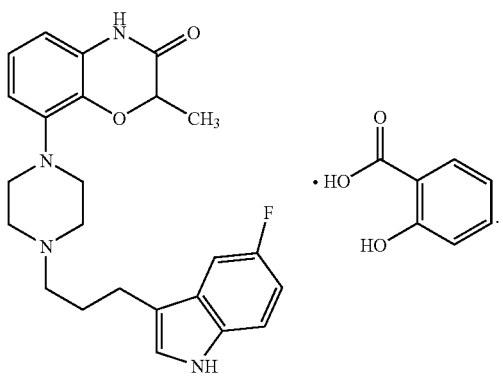

2

2. The compound according to claim 1, wherein said compound is in solid form.

3. The compound according to claim 2, wherein said compound is crystalline.

4. The compound according to claim 3, wherein said compound is a crystalline solid substantially free of amorphous compound 2.

5. The compound according to claim 1, wherein said compound is substantially free of impurities.

6. A method for preparing compound 2:

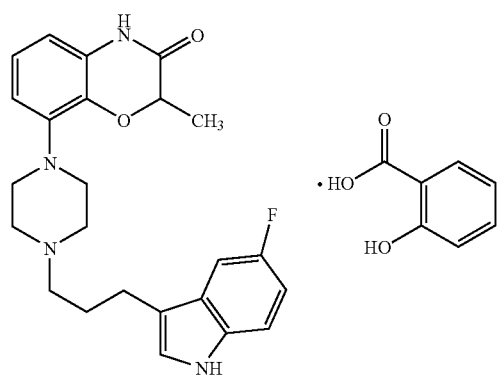

2 comprising the steps of:
providing compound 1:

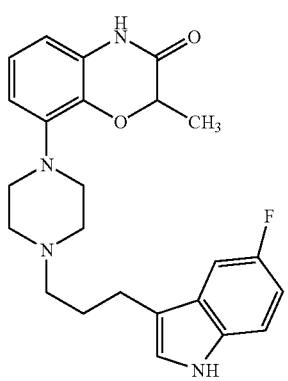

1 combining compound 1 with salicylic acid in a suitable solvent; and
optionally isolating compound 2.

7. The method according to claim 6, wherein said suitable solvent is a protic solvent, a polar aprotic solvent, or a mixture thereof.

8. A method for preparing compound 2:

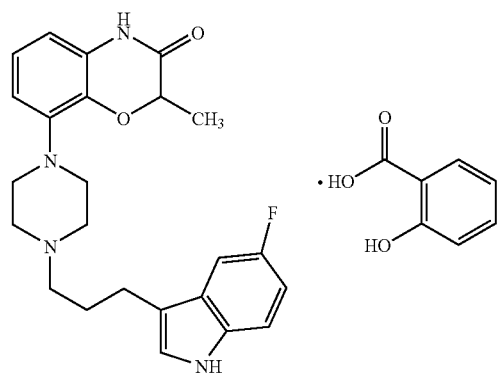

2 comprising the steps of:
combining compound 1:

1 with a suitable solvent and heating to form a solution thereof;
adding salicylic acid to said solution; and
optionally isolating compound 2.

9. Compound 3:

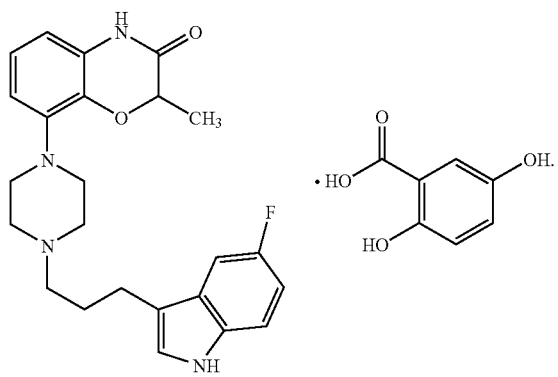

10. The compound according to claim 9, wherein said compound is in solid form.

11. The compound according to claim 10, wherein said compound is crystalline.

12. The compound according to claim 11, wherein said compound is a crystalline solid substantially free of amorphous compound 3.

13. The compound according to claim 9, wherein said compound is substantially free of impurities.

14. A method for preparing compound 3:

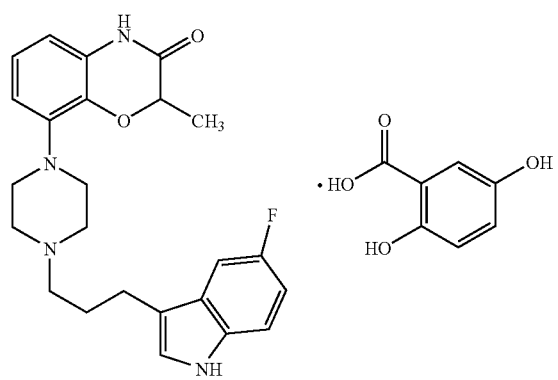

comprising the steps of:
providing compound 1:

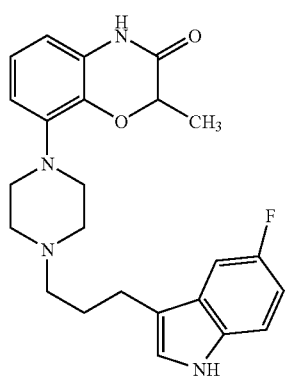

combining compound 1 with gentisic acid in a suitable solvent; and
optionally isolating compound 3.

15. The method according to claim 14, wherein said suitable solvent is a protic solvent, a polar aprotic solvent, or a mixture thereof.

16. A method for preparing compound 3:

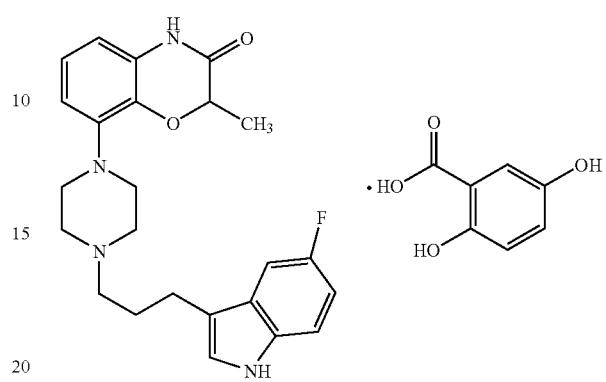

comprising the steps of:
combining compound 1:

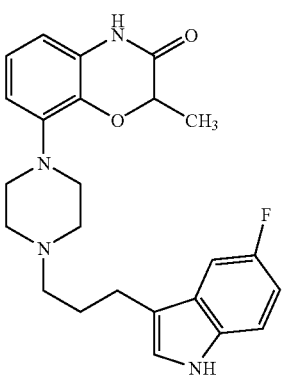

with a suitable solvent and heating to form a solution thereof;
adding gentisic acid to said solution; and
optionally isolating compound 3.

17. A composition comprising:
compound 2:

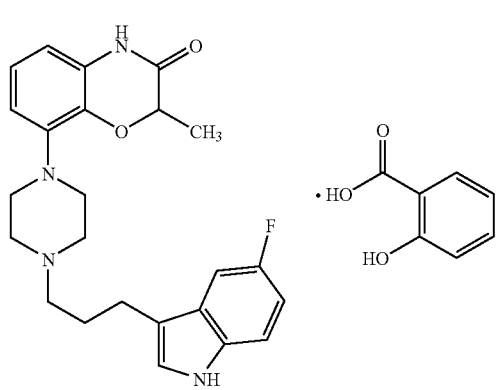

or compound 3:

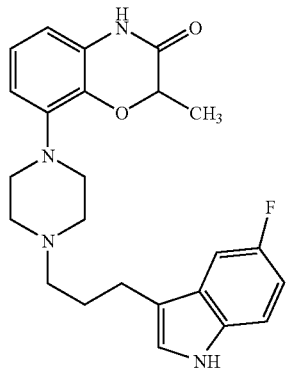 · 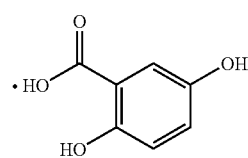

or a mixture thereof, and a pharmaceutically acceptable carrier, adjuvant, or vehicle.

18. The composition according to claim 17, wherein said composition is a delayed release composition.

19. A method of modulating one or more GPCRs in a biological sample, comprising contacting said biological sample with a compound according to either of claims 1 or 9.

20. A method of treating, or lessening the severity of, one or more disorders selected from Parkinson's disease, psychoses depression, anxiety, Huntington's disease, panic disorder, obsessive compulsive disorder, social phobias, aggression or agitation, migraine, scleroderma, Raynaud's phenomenon, emesis, a GI tract disorder related to the regulation of peristalsis, or prolactin secretion arising from tumours of the pituitary gland, wherein said method comprises administering to a patient a composition according to claim 17.

21. The method according to claim 20, wherein said disorder is Parkinson's disease.

22. The method according to claim 20, wherein said disorder is a psychosis selected from schizophrenia, mania, psychotic depression, and bipolar disorder.

23. The method according to claim 20, wherein said disorder is depression, anxiety, panic disorder, obsessive compulsive disorder, or a social phobia.

24. The method according to claim 20, wherein said disorder is aggression or agitation.

25. The method according to claim 20, wherein said disorder is Huntington's disease, migraine, scleroderma, Raynaud's phenomenon, emesis, a GI tract disorder related to the regulation of peristalsis, or prolactin secretion arising from tumours of the pituitary gland.

* * * * *